(12) United States Patent
Hickey et al.

(10) Patent No.: US 10,934,566 B2
(45) Date of Patent: Mar. 2, 2021

(54) HIGH PRODUCTIVITY METHANE FERMENTATION PROCESSES

(71) Applicant: Mango Materials, Inc., Oakland, CA (US)

(72) Inventors: Robert F. Hickey, Okemos, MI (US); Margaret Catherine Morse, Piedmont, CA (US); Allison J. Pieja, Santa Cruz, CA (US)

(73) Assignee: MANGO MATERIALS, INC., Oakland, CA (US)

( * ) Notice: Subject to any disclaimer, the term of this patent is extended or adjusted under 35 U.S.C. 154(b) by 0 days.

(21) Appl. No.: 16/614,673

(22) PCT Filed: May 18, 2018

(86) PCT No.: PCT/US2018/033423
§ 371 (c)(1),
(2) Date: Nov. 18, 2019

(87) PCT Pub. No.: WO2018/213724
PCT Pub. Date: Nov. 22, 2018

(65) Prior Publication Data
US 2020/0181659 A1 Jun. 11, 2020

Related U.S. Application Data
(60) Provisional application No. 62/603,181, filed on May 19, 2017.

(51) Int. Cl.
*C12P 7/62* (2006.01)
*C12F 3/02* (2006.01)

(52) U.S. Cl.
CPC ............... *C12P 7/625* (2013.01); *C12F 3/02* (2013.01)

(58) Field of Classification Search
CPC .................................. C12P 3/02; C12P 7/625
USPC ........................................................ 435/135
See application file for complete search history.

(56) References Cited

U.S. PATENT DOCUMENTS

| | | |
|---|---|---|
| 8,030,021 B2 | 10/2011 | Criddle et al. |
| 8,071,342 B2 | 12/2011 | Herrema et al. |
| 8,795,995 B2 | 8/2014 | Hickey et al. |
| 8,936,927 B2 | 1/2015 | Hickey et al. |
| 9,040,267 B2 | 5/2015 | Herrema |
| 9,062,340 B2 | 6/2015 | Criddle et al. |

(Continued)

FOREIGN PATENT DOCUMENTS

WO  WO/2018/213724  11/2018

OTHER PUBLICATIONS

International Search Report issued in related PCT Application No. PCT/US2018/033423, dated Sep. 13, 2018, 2 pages.

(Continued)

*Primary Examiner* — Deborah D Carr
(74) *Attorney, Agent, or Firm* — McCracken & Gillen LLC

(57) ABSTRACT

Processes are provided for enhancing the productivity of fermenters during the metabolic conversion of methane-containing gases to products containing polyhydroxyalkanoate, which products can be used to make, for instance, animal feed or biodegradable, polymeric articles. The processes involve one or both of attenuating the heat generated to grow a population of microorganisms and removal of heat during the fermentation by removal of carbon dioxide.

24 Claims, 1 Drawing Sheet

(56) References Cited

U.S. PATENT DOCUMENTS

| | | |
|---|---|---|
| 2009/0317879 A1 | 12/2009 | Criddle et al. |
| 2012/0077238 A1 | 3/2012 | Herrema et al. |
| 2013/0052681 A1* | 2/2013 | Criddle .................... C12Q 1/04 435/34 |
| 2013/0337516 A1 | 12/2013 | Herrema |
| 2014/0024872 A1 | 1/2014 | Silverman et al. |
| 2014/0206049 A1 | 7/2014 | Herrema et al. |
| 2015/0111265 A1 | 4/2015 | Lidstrom et al. |
| 2015/0140621 A1 | 5/2015 | Herrema et al. |

OTHER PUBLICATIONS

Pieja et al., Cyclic, alternating methane and nitrogen limitation increases PHB production in a methanotropic community, Bioresource Technology, 2012, pp. 1-8.

Song et al., "Poly-3-hydroxybutyrate production from methanol by Methylosinus trichosporium IMV3011 in the non-sterilized fed-bath fermentation", African Journal of Microbiology Research, vol. 8 (28), Nov. 30, 2011, pp. 5022-5029.

\* cited by examiner

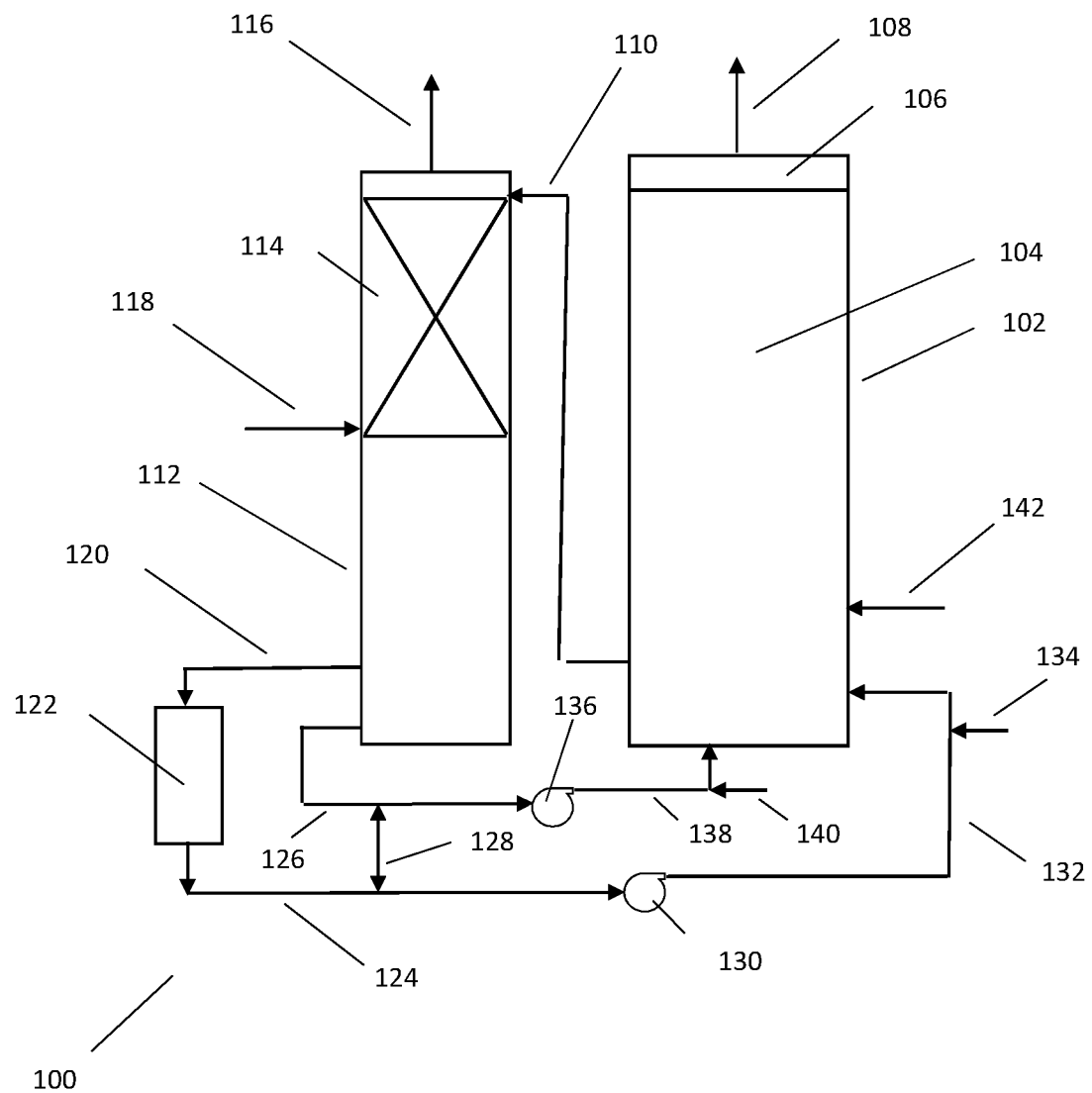

HIGH PRODUCTIVITY METHANE FERMENTATION PROCESSES

REFERENCE TO RELATED APPLICATION AND PRIORITY DOCUMENT

This application claims priority to U.S. Provisional Application 62/603,181 filed May 19, 2017.

FIELD OF THE INVENTION

This invention pertains to high productivity processes for the fermentation of methane by methanotrophs.

BACKGROUND TO THE INVENTION

The fermentation of methane by methanotrophs is well known. Proposals exist for the growth microorganisms on methane-containing gas to produce polyhydroxyalkanoates (PHA) or to produce protein with a modulated PHA-content, e.g., for use as, or as a component of, animal feed. Methane is readily available from fossil sources as well as biological sources. Frequently the price of carbon from methane sources is considerably less expensive than carbon from other sources such as sugars. The ability to convert methane to useful products via its fermentation by methanotrophs offers the potential for economic advantages. Additionally, since the sources of methane-containing gases can be renewable sources such as biogas and landfill gas advantages exist to provide products from rapidly renewable sources.

Polyhydroxyalkanoates can be readily biodegraded and are essentially non-toxic. Thus, PHA has been proposed as a substitute for environmentally persistent plastics. Some studies have indicated that the presence of PHA may have beneficial properties in fish feed. Additionally, PHA can also be a useful component of, for instance, a formulated and extruded or pressed feed pellet.

Polyhydroxyalkanoate-containing products have been made through metabolic processes using sugar feedstocks (including sugars per se and starches and cellulosic materials that can yield sugars through enzymatic activity). Sugar feedstocks are typically significantly more expensive than methane-containing gases and thus attention has been directed to methane as the feedstock. Challenges exist, however, in producing PHA-containing products from methane-containing gases as the solubility of methane in aqueous media is low and high heat is generated by the methanotrophs during the bioconversion of methane. Traditional bioprocesses to produce PHA from methane thus maintain low methanotroph densities in the aqueous broth, which low densities in turn provide low PHA productivity per unit volume of bioreactor. Accordingly, commercially available PHA's have been significantly more expensive than conventional petroleum-based polymers and therefore have not met with widespread commercial acceptance.

In general, the bioprocesses for making PHA-containing products from methane-containing gases comprise the steps of growing a population of methanotrophs ("balanced cell growth") and then subjecting the methanotrophs to environmental conditions that do not support growth of the population of the microorganisms but foster production of PHA by the methanotrophs ("unbalanced cell growth"). Where PHA is the sought product, the PHA is subsequently harvested from the microorganisms. Both methane-containing gas and oxygen-containing gas are supplied to the aqueous broth containing the methanotrophs for the growth of the population of methanotrophs and their production of PHA.

Accordingly a need exists to produce PHA-containing products from methane-containing gases with higher productivities per unit volume of bioreactor. Advantageously, preferred processes would achieve higher productivities in an economically-attractive manner.

SUMMARY OF THE INVENTION

By this invention bioprocesses are provided for making PHA-containing products from methane-containing gases with high productivities. In accordance with this invention, a high density of methanotrophs can be achieved per unit of bioreactor volume without undue cooling costs associated with the substantial exothermic nature of the bioconversion of methane. The processes of this invention facilitate desirable high mass transfer rates of methane from the gas phase to the aqueous broth or medium. These high mass transfer rates support high methanotroph densities. However, high mass transfer rates and high methanotroph densities result in greater generation of heat and greater production of carbon dioxide. The processes of this invention integrate the ability to achieve high methane transfer rates with heat removal to maintain the aqueous medium at suitable temperatures for the bioprocess.

In the processes of this invention, a portion of aqueous medium containing carbon dioxide generated by the methanotrophs is withdrawn from the reaction zone and contacted with a stripping gas to remove dissolved carbon dioxide from the withdrawn aqueous medium (resulting in "carbon dioxide-lean medium or broth"). At least a portion, and preferably essentially all, of the carbon dioxide-lean medium is passed to the reaction zone where it becomes part of the aqueous medium in the reaction zone. The removal of carbon dioxide from the aqueous medium results in increased rates of mass transfer of each of methane and oxygen to the aqueous medium in the reaction zone.

Additionally, during the contact with the stripping gas, the evaporation of carbon dioxide and water from the withdrawn aqueous medium results in cooling the aqueous medium. As the population of methanotrophs increases, so does the generation of carbon dioxide. Accordingly, the heat removed through evaporative cooling due to carbon dioxide vaporization somewhat tracks the population growth of the methanotrophs. The extent of heat removal due to water vaporization will, of course, relate to the relative humidity of the stripping gas. Since water is also formed during the metabolic oxidation of methane to carbon dioxide, the vaporization of water can be beneficial from the standpoint of maintaining a constant volume of aqueous medium during the process.

For purposes herein, the term "limiting substrate" means the one of methane or oxygen that is the more limiting parameter for adequate mass transfer for balanced cell growth and/or unbalanced cell growth at any given time in the process. It is to be understood that during an operation, it is possible for one substrate to be limiting for a period of time and then another substrate to be limiting. In most operations, the mass transfer rate of methane is limiting the balanced cell growth and unbalanced cell growth at high methanotroph densities. However, this invention contemplates modes of operations where oxygen mass transfer is the limiting parameter. For example, as will be discussed in more detail later, one or more of methanol, formic acid or water soluble salt thereof can be added to the aqueous medium, in which case, oxygen mass transfer could become the limiting substrate.

A broad aspect of this invention pertains to high productivity processes for bioconverting methane to product containing polyhydroxyalkanoate, e.g., PHA or protein containing modulated PHA content, comprising (a) passing a methane-containing gas and an oxygen-containing gas to a reaction zone for contact under fermentation conditions with an aqueous medium having a population of methanotrophs therein, said medium containing nutrients for the growth of the population of the methanotroph to provide a methanotroph-rich aqueous medium, said growth of the population of methanotrophs also resulting in the co-production of carbon dioxide, water and heat, and withdrawing unreacted gas from said reaction zone; (b) passing a methane-containing gas and an oxygen-containing gas to a reaction zone for contact under fermentation conditions with at least a portion of the methanotroph-rich aqueous medium, said medium having a limitation, e.g., a substantial absence to create nutrient limited conditions that inhibit the growth of the population of methanotrophs, of at least one nutrient required for the growth of the population of the methanotrophs, to cause production of polyhydroxyalkanoate by the methanotrophs and the co-production of carbon dioxide, water and heat, and withdrawing unreacted gas from said reaction zone; and (c) separating the polyhydroxyalkanoate-containing methanotrophs from the aqueous medium of step (b), wherein for at least a portion of the duration of each of steps (a) and (b):
  i. the rate of passing at least one limiting substrate gas to the reaction zone in each of steps (a) and (b) is (A) at substrate-diffusion conditions and, optionally and preferably, (B) is modulated to provide a substantially stable molar concentration of methane in the unreacted gases;
  ii. in at least one of steps (a) and (b) a portion of the aqueous medium is continuously withdrawn from the reaction zone and contacted with a stripping gas to remove carbon dioxide and provide a carbon dioxide-lean aqueous medium; and
  iii. recycling at least a portion of the carbon dioxide-lean aqueous medium to the reaction zone of at least one of steps (a) and (b).

Preferably substep (ii) is conducted at least during the time that the population of methanotrophs is at least about 8, preferably at least about 10, grams per liter (as measured by dry cell mass), and often at least during a period of time where the population of methanotrophs resides within the range of about 8 and 80, and preferably between about 10 and 60, grams per liter (as measured by dry cell mass).

In another broad aspect of this invention, one or both of methanol and formic acid or water soluble salt thereof ("oxygenated C1 compound") is added to the aqueous broth during either or both of the growth of the methanotrophs or the production of PHA phases. The oxygenated C1 compound serves to provide additional carbon substrate to the methanotrophs and thus maintain population growth of the methanotrophs and production of PHA at a rate beyond that which can be supported by the mass transfer rate of methane from the gas phase to the aqueous medium under a given set of conditions. Additionally, the metabolic conversion of the oxygenated C1 compound is less exothermic than that of methane per carbon atom. Thus, this aspect pertains to high productivity processes for bioconverting methane to product containing polyhydroxyalkanoate comprising (a) passing a methane-containing gas and an oxygen-containing gas to a reaction zone for contact under fermentation conditions with an aqueous medium having a population of methanotrophs therein, said medium containing nutrients for the growth of the population of the methanotrophs to provide a methanotroph-rich aqueous medium, said growth of the population of microorganisms also resulting in the co-production of carbon dioxide, water and heat, and withdrawing unreacted gas from said reaction zone; (b) passing a methane-containing gas and an oxygen-containing gas to a reaction zone for contact under fermentation conditions with at least a portion of the methanotroph-rich aqueous medium, said medium containing an absence of at least one nutrient required for the growth of the population of the methanotrophs to cause production of polyhydroxyalkanoate and the co-production of carbon dioxide, water and heat, and withdrawing unreacted gas from said reaction zone; and (c) separating the polyhydroxyalkanoate-containing methanotrophs from the aqueous medium of step (b), wherein an oxygenated C1 compound of at least one of methanol and formic acid or water soluble salt thereof is supplied to the aqueous medium in at least one of steps (a) and (b). Preferably the oxygenated C1 compound is supplied at least under methane diffusion limited conditions.

A yet further broad aspect of this invention pertains to high productivity processes for bioconverting methane to product containing polyhydroxyalkanoate comprising (a) passing a methane-containing gas and an oxygen-containing gas to a reaction zone for contact under fermentation conditions with an aqueous medium having a population of methanotrophs therein, said medium containing nutrients for the growth of the population of the methanotroph to provide a methanotroph-rich aqueous medium, said growth of the population of methanotrophs also resulting in the co-production of carbon dioxide, water and heat, and withdrawing unreacted gas from said reaction zone; (b) passing a methane-containing gas and an oxygen-containing gas to a reaction zone for contact under fermentation conditions with at least a portion of the methanotroph-rich aqueous medium, said medium containing an absence of at least one nutrient required for the growth of the population of the methanotrophs, to cause production of polyhydroxyalkanoate and the co-production of carbon dioxide, water and heat, and withdrawing unreacted gas from said reaction zone; and (c) separating the polyhydroxyalkanoate-containing methanotrophs from the aqueous medium of step (b), wherein for at least a portion of the duration of each of steps (a) and (b):
  i. the rate of passing at least one limiting substrate gas to the reaction zone in each of steps (a) and (b) is (A) at substrate-diffusion conditions and, optionally and preferably, (B) is modulated to provide a substantially stable molar concentration of methane in the unreacted gases;
  ii. in at least one of steps (a) and (b) a portion of the aqueous medium is continuously withdrawn from the reaction zone and contacted with a semi-permeable membrane to remove carbon dioxide and provide a carbon dioxide-lean aqueous medium; and
  iii. recycling at least a portion of the carbon dioxide-lean aqueous medium to the reaction zone of at least one of steps (a) and (b).

The semi-permeable membrane used to remove carbon dioxide from the aqueous medium for at least one of steps (a) and (b) is preferably a degassing, or pervaporation, membrane permeable to carbon dioxide, and more preferably, the membrane also is permeable to water. The membrane, which may be organic or inorganic, serves as a barrier between the liquid phase and a vapor phase permeate. The driving force for the permeation of carbon dioxide and water is generally characterized as the differential in partial pressure. The partial pressure differential can be at least in part maintained by an absolute pressure differential across the membrane, e.g., the permeate side being under vacuum, and/or a sweep gas on the permeate side of the membrane. The sweep gas can be of the same type as used for stripping. The evaporation of the permeate, which is carbon dioxide and usually water, occurs on the permeate side of the membrane and provides cooling by the latent heat of vaporization.

BRIEF DESCRIPTION OF THE DRAWING

FIG. 1 is a schematic depiction of an apparatus useful in processes of this invention.

DETAILED DISCUSSION

All patents, published patent applications and articles referenced in this detailed description are hereby incorporated by reference in their entireties.

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability.

Biogas means a gas produced from a renewable source of carbon and preferably containing at least about 20 mole percent carbon dioxide. Anaerobically derived gas means biogas produced by the anaerobic digestion or fermentation of organic matter in the absence of oxygen and primarily contains methane and carbon dioxide. Anaerobic digester gas has a typical composition of between about 25 and 50 volume percent carbon dioxide and about 40 and 70 volume percent methane with small amounts of hydrogen, hydrogen sulfide, ammonia, and nitrogen.

Intermittently or intermittent means from time to time and may be at regular or irregular time intervals.

Landfill gas has the typical composition of between about 25 and 60 volume percent carbon dioxide and about 35 and 70 volume percent methane with small amounts of carbon monoxide, hydrogen, hydrogen sulfide, oxygen, and nitrogen.

Limiting nutrient conditions or nutrient limited conditions means that one or more nutrients or micronutrients required for growth of a population of microorganisms is absent to the extent there is a shortage of at least one nutrient required for the growth of the population of the methanotrophs that inhibit the growth of the population of methanotrophs in a reaction zone and increases the levels of polyhydroxyalkanoate compounds in the methanotrophs relative to a reaction zone that receives the at least one nutrient in a suitable amount as required for growth. Substantially absent with respect to the limiting nutrient conditions means that the one or more nutrients required for growth is not present other than in residual or trace amounts or as an impurity in another component introduced into the broth.

A methanotroph is a prokaryote that metabolizes methane as a source of carbon and energy and can be wild type or genetically engineered. The term methanotrophs is intended to include genetically modified microorganisms that might not be a methanotroph in the absence of the genetic modification.

Microbubbles are bubbles having a diameter of 500 microns or less.

Natural gas means a combustible mixture of gaseous hydrocarbons from sedimentary rocks usually containing over 75% methane with minor amounts of 2-4 carbon alkanes or from coal beds where the methane is often present with nitrogen. Natural gas can contain other components such as, and not in limitation, carbon dioxide, hydrogen sulfide, water vapor and nitrogen.

Nutrients and micronutrients are food or any nourishing substance assimilated by a microorganism and required for growth, repair and normal metabolism. Micronutrients are nutrients required in small amounts such as vitamins and minerals as compared to, e.g., carbon, nitrogen and phosphorus sources.

Polyhydroxyalkanoates can be characterized by repeating units of the formula

—[OC(R)H—(CH$_2$)$_m$—C(O)]$_n$— wherein R is hydrogen or lower alkyl of 1 to 6, preferably 1 to 4, carbons; m and n are integers and m is 1 or 2; and a molecular weight (weight average) of from about 10,000 to about 5 million or more Daltons. Examples of polyhydroxyalkanoates include, but are not limited to, polyhydroxybutyrate and polyhydroxyvalerate.

Product containing polyhydroxyalkanoate refers to viable or non-viable methanotrophs or residue of methanotrophic cells that internally and/or externally contain polyhydroxyalkanoate metabolically produced by the methanotroph.

Population of microorganisms refers to the number of microorganisms in a given volume and include substantially pure cultures and mixed cultures.

Proteins are macromolecules containing one or more long chains of amino acid residues, and include, but are not limited to, peptides, oligopeptides and polypeptides, and may contain sulfur in addition to carbon, nitrogen oxygen and carbon atoms.

Single cell proteins are edible, unicellular microorganisms.

Substantial uniformity in liquid phase means that composition of the liquid phase is substantially the same throughout a bioreactor. Usually the concentration of a component is within about 5 percent of its average concentration in a uniform liquid phase, that is, if the average concentration of a component is 55.3 molar percent, then a substantial uniformity would mean that the component can, for example, vary between about 52.5 and 58.0 molar percent.

Substantial non-uniformity in the gas phase means that the mass (both in the gas bubbles and dissolved gases) of at least one component provided by the gas substrate changes by at least 50 mass percent between the point of entry of the gas into a bioreactor and the point that the gas emerges from the broth.

Substrate diffusion conditions means that for balanced cell growth conditions (step (a)), the rate of mass transfer of both methane and oxygen are not in and of themselves alone, materially adversely affecting the rate of growth of the methanotroph population; and for unbalanced cell growth conditions (step (b)), the rate of mass transfer of both methane and oxygen are not in and of themselves alone, materially adversely affecting the methanotroph population. The term "materially" means that the adverse effect for (1) balanced cell growth conditions is that the population of methanotrophs continues to grow, and for (2) unbalanced cell growth conditions is that the mass transfer of both methane and oxygen is sufficient to at least maintain the population of methanotrophs, i.e., the population of methanotrophs does not decrease by more than 20, preferably by not more than 10, mass percent. In some instances, during balanced cell growth conditions the population of methanotrophs continues to grow at less than 20, preferably less than 10, mass percent of the projected exponential growth rate for the given cell density.

Substrate diffusion limiting conditions means that the rate of diffusion of at least one of methane and oxygen to the broth containing the methanotrophs is other than at substrate diffusion conditions. It is to be understood that substrate diffusion conditions and substrate diffusion limiting conditions are affected by driving forces for the mass transfer as well as physical constraints such as bubble size and duration of the bubble in the broth.

All references to mass of cells is calculated on the basis of the dry mass of the cells. Dry mass is determined by filtration of the microorganisms from the broth, followed by washings with deionized water, and drying at a temperature of about 103 to 105° C. in an oven and cooling in a desiccator. The drying and cooling in a desiccator should be repeated for a given sample until the mass of the sample remains constant.

References to organic acids herein shall be deemed to include corresponding salts and esters.

Polyhydroxyalkanoates are produced by methanotrophs for energy storage. As is well known in the art, the rate of PHA production increases when the methanotroph is placed under stress. Stress can be induced through the use of limiting nutrient conditions but some oxygen and methane or oxygenated C1 compound still need to be provided to maintain the methanotrophs. The processes of this invention are widely applicable to a broad range of methanotrophs that are capable of producing PHA. As set forth in the definition, methanotrophs include genetically modified microorganisms that are able to consume methane although not traditionally characterized as a methanotroph.

Methanotrophs can be obtained from a wide variety of sources. Methanotrophs are found in environments where both oxygen and methane are present, often at the interface between aerobic and anaerobic zones. They are common in rice paddies, swamps and marshes, surface sediments in ponds and lakes, activated sludge, and meadow and deciduous forest soils, including freshwater, brackish, and saline environments, deserts, landfills, coal mine surfaces, and oceans. Preferable sources include those environments subject to periodic stress, such as carbon, nutrient, or oxygen limitation. The use of mixed bacterial cultures makes the process less expensive as compared with processes that use pure cultures by eliminating the need for maintenance of special cultures. In the context of the present description, the term "mixed cultures" is defined to include bacterial communities containing a variety of distinct cultures or species, irrespective of whether or not the species are well-defined. The term "mixed cultures" also includes enrichment communities. These are communities of organisms subjected to selective pressures favorable for the growth of organisms that positively affect PHA production and unfavorable for the growth of organisms that negatively affect PHA production. Selection techniques can be used to enrich the population of methanotrophs in a mixed culture to that providing the sought PHA.

Examples of methanotrophs include, but are not limited to, *Methylosinus, Methylocystis, Methylocella, Methylocapsa, Methyloferula, Methylomonas, Methylobacter, Methylococcus, Methylomicrobium, Methylosphaera, Methylocaldum, Methylosarcina, Methylothermus, Methylohalobius,* *Methylogaea, Methylosoma, Methylomarinum, Methylovulum, Methyloacidiphilum, Creonthrix,* and *Clonothrix.* Different methanotrophs will differ in how rapidly PHA is accumulated, and different methanotrophs will likely produce PHA with differing polymers or molecular weight distributions. Thus the selection of the methanotrophs is typically targeted for the particular PHA sought. See for instance, U.S. Pat. No. 8,030,021, herein incorporated by reference in its entirety.

Methanotrophs contain proteins and are generally edible, especially after denaturing, and thus are suitable as single cell protein sources. Proteins included in methanotrophs include, but are not limited to:

| Protein | Range, mass percent of dried methanotroph | Frequent Range, mass percent of dried methanotroph |
| --- | --- | --- |
| alanine | 1 to 10 | 2 to 7 |
| arginine | 1 to 5 | 2 to 5 |
| aspartic acid | 2 to 10 | 3 to 7 |
| glutamic acid | 3 to 10 | 3 to 8 |
| glycine | 1 to 7 | 2 to 5 |
| histidine | 0.5 to 5 | 0.5 to 2 |
| isoleucine | 1 to 5 | 1 to 4 |
| leucine | 2 to 10 | 3 to 7 |
| lysine | 1 to 5 | 2 to 5 |
| methionine | 0.01 to 1 | 0.05 to 0.5 |
| phenylalanine | 1 to 5 | 2 to 5 |
| proline | 1 to 5 | 2 to 5 |
| serine | 1 to 5 | 1 to 4 |
| threonine | 1 to 5 | 1 to 4 |
| tyrosine | 0.5 to 5 | 1 to 3 |
| valine | 1 to 7 | 2 to 5 |

The protein often constitutes about 30 to 80 mass percent of the dry cell with the remainder being fat (often between about 2 and 15, say, 3 and 12, mass percent), PHA (often between about 5 to 50 mass percent for animal feed and about 10 and 50 mass percent where PHA is the sought final product) and other components (between about 5 and 20 mass percent). Although in some instances a cell may express protein, for practical purposes the protein is contained in the cells and/or on the surface of cells. Thus, the growth of the population of the methanotrophs is somewhat proportional to the production rate of protein.

The processes of this invention are also applicable to a wide variety of methane-containing gases including, but not limited to, natural gas, methane gas from coal and biogas (including, but not limited to, anaerobic digester gas and landfill gas), tail gas from other processes, e.g., a tail gas derived directly or indirectly from another fermentation process, and mixtures thereof. Typically the methane concentration in the methane-containing gas fed to the reaction zone is at least about 10 mole percent, and often is in the range of about 15 to 99 to essentially 100, mole percent. The methane-containing gas may contain other components such as, but not in limitation, higher alkanes, nitrogen, carbon dioxide, hydrogen sulfide, siloxanes and water vapor. Any components in the methane-containing gas that may be toxic to or impair the performance of the methanotrophs are preferably removed or reduced in concentration to levels acceptable to the methanotrophs.

The methane-containing gas and an oxygen-containing gas are fed to an aqueous medium (broth) containing methanotrophs. Preferably the methane-containing gas and the oxygen-containing gas are introduced into the bioreactor in the form of microbubbles. Often the microbubbles have diameters in the range of 0.01 to 0.5, preferably 0.02 to 0.3 millimeter. Preferably the methane-containing gas and the oxygen-containing gas are separately injected into the broth using a motive fluid. Variations in the motive liquid flow rate can be used to modulate the microbubble size and thus modulate the rate of transfer of methane and oxygen to the broth. If desired, surface active agents can be used to help reduce the size of the bubbles.

The rate at which each of the methane-containing gas and the oxygen-containing gas is fed to the broth can vary widely but is typically dependent upon assuring that adequate amounts of dissolved methane and oxygen are available to the methanotrophs. During the growth of the population of methanotrophs, the demands for methane and oxygen per unit volume of the reaction zone will proportionately change to the increase in density of the methanotrophs. Accordingly, the rates of supply of these gases preferably are modulated based upon the density of methanotrophs and desired population growth rate and/or PHA accumulation. A significant cost in the production of single cell protein has prior to this invention resided in the separation, dewatering and drying of the methanotrophs to provide the animal feed. Similarly, higher densities of methanotrophs in broths facilitate the recovery of PHA from the methanotrophs where purified PHA is the sought final product. As can be readily appreciated, the processes of this invention enable the achievement of higher methanotroph densities in the broth due to the increased ability to transfer methane and oxygen to the aqueous broth and the ability to remove heat from the bioreactor.

By adjusting the rate of supply of methane, the loss of methane in the unreacted gases passing from the broth can be minimized. The rate of supply of methane-containing gas to the reaction zone at least during a portion of the process is such that the unreacted gases contain a substantially stable molar concentration of methane (preferably the molar concentration of methane does not vary by more than 20, more preferably by more than 10, percent of the average methane molar concentration). If the unreacted gases are to be sent to waste, e.g., burned in a flare or thermal oxidizer, economical operation improves with lower methane concentrations in the unreacted gases although natural gas may be required to maintain the thermal oxidation. Often facilities that generate methane-containing gas, such as anaerobic digesters, have flare or other thermal oxidation unit operation that may be available to the PHA production operation. Preferably, where the unreacted gases are sent to waste, at least about 70, and preferably at least about 80, and sometimes between about 85 and 99 to essentially all, the methane in the methane-containing gas is metabolized in the reaction zone. Preferably, the rate of passing methane-containing gas to the reaction zone is modulated to provide a withdrawn unreacted gas containing less than 10 mole percent methane.

On the other hand, if the unreacted gases are to be used for energy, the molar concentration of methane should be sufficiently high to achieve a desired heat content. Hence, in some embodiments, the unreacted gases may contain 25 or more volume percent methane. The unreacted gases will also contain carbon dioxide produced from the metabolic activity, which may or may not need to be removed. In either event, the rate of supply of the methane-containing gas to the reaction zone is modulated to provide a substantially stable molar concentration of the methane in the unreacted gases. It should be appreciated that the unreacted gases will serve to remove heat from the reaction zone, and may serve to strip out undesired gases that may be dissolved in the aqueous medium. If desired, the rate of supply of the methane-containing gas can be modulated based upon desired heat removal or stripping of undesired, dissolved gases.

Additionally, the aqueous medium can be used to remove from the methane-containing gas other gaseous components contained therein especially where the unreacted gas stream is to be used for other purposes such as the generation of power or feedstock for another biological or chemical process. The removal of adverse components may render the unreacted gas stream directly suitable for such further use or reduce the amount of pretreatment. The removed components can then be recovered from the aqueous medium. Components that can be removed by the aqueous medium include, but are not limited to, hydrogen sulfide and dimethyl siloxane, both of which can be adverse in feedstocks for combustion and many catalytic chemical processes. For example, the methane-containing feed contains hydrogen sulfide and the aqueous medium absorbs at least a portion of the hydrogen sulfide to provide an unreacted gas stream containing a reduced concentration of hydrogen sulfide.

The rates of mass transfer of methane and oxygen from the gas phase into the broth will depend upon the partial pressure driving force for each gas. Each of methane and oxygen has limited solubility in water, and reducing the mass of carbon dioxide in the broth beneficially improves the driving force for mass transfer of methane and oxygen to the broth. In accordance with this invention, for at least a segment of the duration of the process, a portion of the broth is continuously withdrawn from the reaction zone and contacted with a stripping gas to remove dissolved carbon dioxide and provide a carbon dioxide-lean aqueous medium, or broth, for recycle to the reaction zone. In some instances, this continual withdrawal and stripping occurs over the full duration of the process, and in other instances, it occurs at least when the density of methanotrophs in the broth is at least about 2, say, at least about 5, and frequently at least about 10, grams per liter. The methanotrophs can be entrained with the withdrawn broth or can be removed from the broth prior to being passed to the stripping unit operation.

The rate of withdrawal of the broth is often sufficient to remove an amount of carbon dioxide equivalent to at least about 35, preferably at least about 40, and in some instances between about 50 and 75, percent of the carbon dioxide produced by the metabolic activity in the reaction zone. It should be understood that the methane-containing feed can, in some instances such as where the methane-containing feed is biogas, contain carbon dioxide.

The calculation of the portion of carbon dioxide removed during stripping is on a mass balance basis taking into account carbon dioxide produced by metabolic activity and carbon dioxide fed to the reaction zone with substrate and other nutrients. For purposes of calculation, the mass of carbon dioxide produced by metabolic activity is based on the assumption that both methane and oxygenated C1 compounds can result in the generation of carbon dioxide. A portion of methane and oxygenated C1 compound can go to cell formation, PHA production and other metabolically-generated components.

In a preferred aspect of this invention, the methane in the withdrawn broth undergoes sufficient further metabolic activity prior to the stripping such that the carbon dioxide-laden gases from the stripping contain less than 20, preferably less than 10, parts per million by volume of methane. In this preferred aspect of the invention the supply of oxygen should be sufficient that the withdrawn broth has sufficient dissolved oxygen to support the metabolic activity.

Any suitable stripping gas can be used in the processes of this invention. Air is a readily available gas to effect stripping. The stripping gas to be used for the stripping when contained in the broth being subjected to stripping can be at any suitable temperature that does not adversely affect the methanotrophs, e.g., between about 10° C. to 50° C., say, 20° C. to 45° C. In many instances it is preferred to maintain the relative humidity of the stripping gas at less than 50, more preferably less than about 25, percent to take advantage of cooling by vaporization of water.

Preferably the stripping is under conditions such that at least 50, more preferably at least about 65, and often at least about 75, percent of the carbon dioxide in the withdrawn broth is stripped. Although higher or lower temperatures can be used, the stripping is typically conducted at the temperature of the withdrawn broth. During stripping, the temperature of the broth is reduced primarily due to both carbon dioxide vaporization and water vaporization. Often during at least a portion of the process, especially during times of peak cooling needs, the carbon dioxide-lean broth from the stripping is at least about 0.25° C., and sometimes, at least about 0.75° C., cooler than the bulk temperature of the broth in the reaction zone.

In one mode, all or a portion of the withdrawn broth comes from a lower portion of the reaction zone where the dissolved carbon dioxide concentration is higher. If desired, the withdrawn broth, which is at a pressure that is at least partially defined by the head of aqueous medium at the point of removal, can be subjected to flashing conditions including a lower pressure, e.g., at ambient pressure, to remove a portion of the carbon dioxide prior to being subjected to stripping.

As stated before, the stripping, if desired, need not be used until the population of methanotrophs reaches a density in the broth that the mass transfer of methane from the gas to the broth is not adequate to maintain the growth of the population or production of PHA or other cooling unit operations are not sufficient to prevent the build-up of temperature in the reaction zone. Alternatively, the rate of withdrawal of broth for stripping can vary with the population growth. As the population of methanotrophs approaches the sought maximum density the rate at which the broth is withdrawn for carbon dioxide stripping often ranges between about 0.5 and 10, say, 1 and 5, times the volume of the broth in the reaction zone per hour.

The broth contains nutrients for the methanotrophs. The process proceeds by first increasing the population of the methanotrophs in what is sometimes referred to as the balanced cell growth phase where the feedstocks and all the nutrients are present in the ratios required to make the macromolecular components of the cell. In other words, no feedstock or nutrient limits the synthesis of proteins, complex carbohydrate polymers, fats, or nucleic acids. Then, the methanotrophs are subjected to limiting nutrient conditions, that is, in unbalanced cell growth phase in which oxygen or at least one nutrient (other than methane or oxygenated C1 compound) needed to make one or more of the macromolecules for growth is not present in the ratio required. Under these conditions, an acceleration of the accumulation of polymers occurs. These polymers include intracellular storage products such as one or more PHAs or secreted products such as extracellular polysaccharide. Usually the limiting nutrient conditions are achieved by providing insufficient amount of nitrogen-compound to support balanced cell growth. Other nutrients that can be restricted or modulated to achieve unbalanced cell growth include, but are not limited to, calcium, phosphorus, sodium, magnesium, iron, copper, boron, zinc, aluminum, nickel, sulfur, molybdenum, manganese, and potassium.

The broth is maintained under suitable conditions for the rapid growth of the population of microorganisms during the balanced cell growth phase and for the production of PHA during the unbalanced cell growth phase. These conditions include temperatures suitable for the methanotrophs, which are usually mesophilic, for instance, between about 25° C. to 45° C., and most frequently between about 28° C. to 42° C.

The balanced cell growth conditions are maintained for a time sufficient to achieve a desired density of methanotrophs in the broth. In most instances, the methanotrophs achieve a density in the broth of at least about 8, preferably at least about 10, grams per liter (calculated on a dry cell basis). Although high densities are desired, practical limitations exist. For example, the population of microorganisms in the broth can increase to the level at which insufficient methane and oxygen can be provided to the broth during balanced cell growth conditions for achieving additional growth of the population (substrate diffusion limiting conditions). Also, the metabolic processes are exothermic, and thus the ability to remove heat from the reaction zone can become a limitation. Therefore, the density of methanotrophs at the end of the balanced cell growth phase is usually at least about 8, say, at least about 10, grams per liter in the broth, and may be as high as 60 or 80 or more grams per liter in the broth.

An advantage of the processes of this invention is the flexibility given to the operator to obtain high densities of methanotrophs at the conclusion of the balanced cell growth conditions due to being able to achieve high methane and oxygen mass transfer from the gas phase to the broth, and thus maintain substrate diffusion conditions at high densities of methanotrophs in the broth. Accordingly, in preferred embodiments, the balanced cell growth conditions are maintained at least until substrate diffusion limitation conditions can no longer be maintained, are nearly reached. Hence, the densities of methanotrophs in the broth are sometimes in the range of about 20 to 80 or more, often in the range of 20 to 60, grams per liter (calculated on a dry cell basis).

In one aspect of this invention, an oxygenated C1 compound is introduced into the broth to supplement the methane feed. Preferably, the oxygenated C1 compound is derived from a renewable resource. The oxygenated C1 compounds are soluble in the aqueous medium of the broth and thus no mass transfer limitations between a gas phase and the aqueous medium affect the rate at which the oxygenated C1 compound can be introduced into the broth. When using an oxygenated C1 compound, additional growth of the population of microorganisms can be obtained under methane diffusion limitation conditions. The oxygenated C1 compound can be added at any time during either or both of the balanced cell growth phase and the unbalanced cell growth phase. The oxygenated C1 compound can be added continuously or intermittently, and may only start to be added as the process nears the transition between methane diffusion conditions and methane diffusion limitation conditions. As oxygenated C1 compound is typically rapidly metabolically consumed by the methanotrophs, achieving good dispersion throughout the fermenter is preferred as well as adding the oxygenated C1 compound intermittently or continuously during all or portions of the fermentation process. The oxygenated C1 compound is preferably used during the unbalanced cell growth phase.

The amount of oxygenated C1 compound provided to the broth can vary widely with still obtaining desirable enhancements to cell growth and methane conversion to PHA. In general, the oxygenated C1 compound is provided in an amount of about 10 to 200, say, 30 to 150, and sometimes between about 50 and 110, grams per kilogram of sought cell mass from the fermentation. The concentration of oxygenated C1 compound in the broth should be maintained below that which adversely affects the methanotrophs. Consequently, it is preferred to continuously or intermittently add oxygenated C1 compound to the broth at a rate commensurate to provide the sought amounts oxygenated C1 compound yet maintain a concentration below that which adversely affects the methanotrophs.

By way of example, and not in limitation of this invention, comparative experiments are conducted to illustrate the effect of oxygenated C1 compound on the population growth of the methanotrophs and the production of PHA. Two fermenters are used for the experiments and are operated in parallel attempting to maintain the same conditions during the fermentation except for the oxygenated C1 compound (methanol) content. The fermenters are stirred, laboratory-scale (4 liters) and do not use the aspect of this invention involving the stripping of carbon dioxide from the broth. Rather, the experiments are intended to illustrate the effect of methanol in the fermentation. The fermentations are conducted at about 30° C. and pH of about 7 (maintained by addition of base, ammonium hydroxide, during the growth phase and potassium hydroxide during the PHA-production phase) for a duration of about 50 hours. The methanotroph is a mixture containing *M. parvus* OBBP. A conventional, aqueous medium containing nutrients is used (nitrate salts medium W1 as described in Peija, et al., Poly-3-hydroxybutyrate metabolism in the Type II methanotroph Methylocystis parvus OBBP. Appl. Environ. Microbiol. 77 (17), 6012-6019). The unbalanced cell growth phase nutrient withdrawn is nitrogen.

The examples provide the following. In the absence of methane feed, substantially no PHA (poly-3-hydroxybutyrate) is generated where methanol is present. The addition of methanol increases the rate of growth of the methanotroph population as compared to the control having an absence of methanol in the broth. The methanol runs consume less oxygen to provide a given cell population and PHA concentration. Increasing the methanol concentration, increases the concentration of PHA and cell population. In all runs, the methanol is fully consumed. See Table I.

the methanotrophs. Typically, the unbalanced cell growth phase is at least about one, preferably at least about 5, and sometimes at least about 8, hours, say, between about 5 and 48, and in some instances, between about 5 and 24, hours.

At the conclusion of the unbalanced cell growth phase, the methanotrophs can be harvested for the recovery of PHA. Any suitable process for recovery of PHA from the methanotrophs can be used. Where a single cell protein is the sought final product, at the conclusion of the unbalanced cell growth phase, the methanotrophs are harvested. Typically, the solids containing the cells are separated and dewatered. Drying of the solids is usually done to stabilize the protein content of the single cell protein product.

The processes of this invention may be continuous, semi-batch or batch. In continuous processes it is preferred to use at least two bioreactors in flow sequence, the first being for the growth of population of the methanotrophs, and the second in flow sequence being for the unbalanced cell growth phase to produce PHA. In a batch process, one or more bioreactors may be used, each can be cycled between balance cell growth conditions and unbalanced cell growth conditions, or alternatively one or more bioreactors may be dedicated to balanced cell growth and the broth containing the methanotrophs passes to a separate bioreactor dedicated to unbalanced cell growth. The latter is generally referred to as a "mother" and "daughter" bioreactor system. In a preferred semi-batch process, one or more mother bioreactors are continually growing the population of methanotrophs. A portion of the broth is intermittently withdrawn from a mother bioreactor and is passed to one of a plurality of daughter bioreactors. The portion of the broth withdrawn from the mother reactor preferably permits a sufficient portion of the broth to remain in the mother reactor for the population of methanotrophs to quickly achieve the density sought for commencing the unbalanced cell growth. For example, the portion withdrawn could leave about 25% by volume of the broth in the mother bioreactor which would result in achieving the sought density for the unbalanced cell growth in about two doublings of the population. Frequently, the volume of broth remaining in the mother bioreactor is at least about 10 volume percent, say, between about 20 and 50 volume percent. The number of daughter bioreactors per mother bioreactor for the semi continuous process is typically between 2 and about 10. Thus, the daughter bioreactors

TABLE I

| | Reactor 1 | | | Reactor 2 | | |
|---|---|---|---|---|---|---|
| Example | OD 600 maximum | PHA % maximum | Total methanol added, grams[b] | OD 600 maximum | PHA % maximum | Total methanol added, grams[b] |
| 1 | 42 | 37 | 0 | 55 | 49 | 101 |
| 2[a] | 42 | n/a | 0 | 22[b] | 15 | 27 |
| 3 | 37 | 41 | 0 | 52 | 50 | 74 |
| 4 | 33 | 34 | 0 | 56 | 55 | 76 |
| 5[c] | 79 | 54 | 0 | 81 | 51 | 141 |
| 6 | 47 | 39 | 84 | 52 | 52 | 209 |

[a]Reators are inoculated at an OD 600 of about 22. No methane is added after inoculation.
[b]In examples 1 and 2 about 4 grams of methanol are added initially and then the remaining methanol is substantially uniformly added over the duration of the run. In examples 3 through 6, all the methanol is continuously added over the duration of the example.
[c]The cell growth rate with methanol is more rapid than that without methanol; however, over the duration of the run, the control reaches the cell population and PHA concentration of the reactor with methanol present.

The duration of the balanced cell growth phase will depend upon the concentration of the inoculum in the broth, the sought density of methanotrophs at the conclusion of the balanced cell growth phase, and the rate of reproduction of can in combination provide a relatively continuous supply of cells for recovery of product containing PHA.

Each bioreactor may be of any suitable configuration including, but not limited to, deep tank bioreactors (e.g., deep tank, bubble column bioreactors); jet loop bioreactors; stirred tank bioreactors; trickle bed bioreactors; biofilm bioreactors; moving bed bioreactors; membrane bioreactors and static mixer bioreactors including, but not limited to, pipe bioreactors. If desired, two or more bioreactors may be used for the balanced cell growth and for the unbalanced cell growth, and these bioreactors may be of similar or different design. For example, a stirred tank bioreactor may be followed by a deep tank bioreactor. Where high conversion of the methane in the methane containing gases is sought, deep tank bioreactors are preferred. Deep tank bioreactors are characterized as having a depth of at least about five, and preferably at least about 10, meters and can be operated to provide a substantially non-uniform gas composition over the depth of the broth contained in the bioreactor and a substantially uniform composition of the broth throughout the bioreactor. Deep tank, bubble column bioreactors are deep tank bioreactors where the methane-containing gas and oxygen-containing gas are introduced as small bubbles in the lower portion to promote mixing. Preferably each of the methane-containing gas and oxygen-containing gas feed is introduced in the form of microbubbles having diameters in the range of 0.01 to 0.5, preferably 0.02 to 0.3 millimeter. The use of eductors or injectors using motive fluids are preferred to form the microbubbles. In many instances, methanotrophs suffer little damage when passed through eductors or injectors, and therefore in these instances the methanotrophs need not be removed prior to reintroducing the carbon dioxide-lean broth to the bioreactor.

Any suitable equipment can be used to strip carbon dioxide from the withdrawn broth. Examples of such equipment include spray towers, bubble columns, and packed or structured columns or degassing membranes. Due to low pressure drop, packed or structured columns are preferred.

Although the stripping of carbon dioxide from the withdrawn broth effects removal of heat from the exothermic metabolic activity, typically additional cooling capacity is required to prevent undue exotherms during the balanced cell growth phase and unbalanced cell growth phase. Often, as the density of cells in the bioreactor approaches the desired maximum concentration, the cooling of the withdrawn broth during the carbon dioxide stripping constitutes the removal of between about 10 and 50, say, between about 15 and 40, percent of the heat removal required to maintain the bioreactor under isothermal conditions. The ancillary heat transfer unit operations required to maintain isothermal conditions can be one or more of direct and indirect heat exchange Direct heat exchange, for instance in a continuous process, can be provided by the continuous addition of cool makeup water to replace the broth continuously removed from the bioreactor.

A general understanding of the invention and its application may be facilitated by reference to the drawing. The drawing is not in limitation of the broad aspects of the invention. The drawing is a schematic depiction of an apparatus generally designated as 100 suitable for practicing the processes of this invention. The drawing omits minor equipment such as pumps, compressors, valves, instruments and other devices the placement of which and operation thereof are well known to those practiced in chemical engineering. The drawing also omits ancillary unit operations. The process and operation of the apparatus of the drawing are described in context of the use of anaerobic digester biogas and air for the production of polyhydroxybutyrate and air for the stripping of carbon dioxide. The process is readily adaptable to using other methane-containing gases, oxygen-containing gases and stripping gases as well as the production of other PHA polymers and single cell protein products.

Bioreactor 102 is a deep tank, bubble column reactor and contains broth 104. In this depicted apparatus, bioreactor 102 is used both for balanced cell growth and unbalanced cell growth. Above the broth 104 resides head space 106 and exhaust line 108 for the removal of unreacted gases from the bioreactor. The unreacted gases may be used for generating heat or sent to waste.

A portion of the broth in bioreactor 102 is passed via line 110 to stripper 112. In line 110 methane dissolved in the withdrawn broth continues to be metabolized by the methanotrophs such that the withdrawn broth passed into stripper 112 contain little if any dissolved methane. As shown, stripper 112 contains structured packing 114. Line 110 distributes the broth on the top of structured packing 114 for contact with stripping gas which for purposes of this discussion is air supplied by line 118 at the bottom of the structured packing. The carbon dioxide-laden stripping gas exits stripper 112 via line 116. A portion of the carbon dioxide-depleted broth collects in the bottom of stripper 112 for passage via line 120 to indirect heat exchanger 122. Line 124 withdraws the broth from indirect heat exchanger 122. Another portion of the carbon dioxide-depleted broth is withdrawn via line 126. The relative amounts of the portion of the carbon dioxide-depleted broth passing to heat exchanger 122 and the portion of the carbon dioxide-depleted broth passing to line 126 will depend upon the desired bulk temperature of the portions. For instance, during the early stages of the balanced cell growth, the cooling effected in stripper 112 may require that not all of the carbon dioxide-depleted broth be subjected to ancillary cooling in heat exchanger 122. Bypassing a portion of the carbon dioxide-depleted broth results in a combined bulk temperature of the broth being returned to bioreactor 102 appropriate for maintaining the temperature of the broth in bioreactor 102 at a constant temperature. Later in the balanced cell growth, substantially all of the carbon dioxide-depleted broth is passed to heat exchanger 122 to maintain isothermal conditions in bioreactor 102. Alternatively, during the earlier portion of the process, a portion of the carbon dioxide-laden stripping gas from line 116 is admixed with the stripping gas supplied by line 118 to reduce the driving force for vaporization of carbon dioxide in the broth. Since less carbon dioxide vaporization would occur, cooling is reduced.

Heat exchanger 122 can be of any suitable design. This invention contemplates that the heat exchanger is in combination with a heat pump where the heat pump provides higher temperature fluid for use in this process or another process. In some instances, the heated fluid from the heat pump can be used for indirect heat exchange with the stripping gas, e.g., air, to reduce its humidity and permit more water to be evaporated during the stripping and thus generate more evaporative cooling. Alternatively, the heated fluid can be used to reduce the heat energy required for recovery of PHA from the cells.

As will be described later, the recycle broth is used as motive fluid for the introduction of methane-containing gases and oxygen-containing gases to bioreactor 102. Line 128 serves to balance the flow rates of the recycling broth in each of the lines 126 and 124 as required as motive fluid.

The broth being recycled in line 124 is passed to pump 130 and then through line 132 for return to bioreactor 102. The broth in line 128 is passed to pump 136 and then to line 138 for return to bioreactor 102. The methane-containing gas and oxygen-containing gas can be introduced into bioreactor 102 in any convenient manner. The use of injectors (gas-liquid eductors) is particularly attractive in that very fine bubbles can be generated at relatively low energy consumption. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the broth itself including, but not limited to its static liquid depth. In some instances the microbubbles, which form a less dense gas-liquid dispersion and any motive fluid used to generate the microbubbles, can facilitate liquid mixing in a bioreactor. The large cross-sectional dimension of the injectors provides several benefits in addition to being able to produce microbubbles. First, they are not prone to fouling since broth is used as the motive liquid as would be a sparger designed to produce microbubbles. Second, the energy required to provide microbubbles of a given size is often less than that required to form microbubbles of that size using a microbubble sparger. Third, a high turn down ratio can be achieved. And fourth, the microbubble size can be easily varied over a wide range. Oxygen-containing gas is supplied to the injectors via line 134 and methane is supplied to the injectors via line 140.

Nutrients and makeup water are supplied to broth 104 in bioreactor 102 via line 142.

By way of illustration and not in limitation, in operation, bioreactor 102 is a 60,000 liter fermenter filled with broth to about 10 meters in depth and inoculated with methanotrophs. It is not essential that bioreactor 102 be sterilized prior to the inoculation. Biogas at a rate of 1850 liters per minute and containing about 23 mole percent methane is passed to bioreactor 102. As the population of methanotrophs increases, if not already to the full volume, additional water and/or nutrients and other additives can be added via line 142 either continuously or intermittently to increase the volume of the broth relatively proportionate with the increase in the population of methanotrophs. The flow of methane-containing gases and oxygen-containing gases is commenced at the time of inoculation of the broth or immediately before the inoculation. Where the gases are introduced using an injector, it is usually preferred to withdraw a portion of the broth from bioreactor 102 to be directly or indirectly passed to each of pumps 130 and 136 to supply the motive fluid (not depicted).

When the population of the methanotrophs is increased to the point where it is desired to remove carbon dioxide from the broth to enhance mass transfer of methane and oxygen to the liquid phase, about 4500 liters per minute of the broth is passed via line 110 to stripper 112. About 135,000 liters (standard temperature and pressure) of air is passed to stripper 112 via line 118, and about 99 percent of the dissolved carbon dioxide in the broth is removed. As stated before, dependent upon the temperature in the bioreactor, the carbon dioxide-depleted broth is removed via one or both of lines 120 in 126 for recycle to bioreactor 102. In comparison with a process conducted without stripping of carbon dioxide from the broth, the evaporative cooling requirement is reduced by about 47 percent at peak cooling requirements and the driving force for methane mass transfer to the broth is increased by about 35 percent.

When the density of methanotrophs in the broth in bioreactor 102 reaches a desired level, the operation of bioreactor 102 is switched to unbalanced cell growth by changing the composition of nutrients supplied to bioreactor 102 via line 142. At the conclusion of the unbalanced cell growth phase, the methanotrophs are harvested and PHB recovered.

It is claimed:

1. A high productivity process for bioconverting methane to product containing polyhydroxyalkanoate comprising (a) passing substrate gas comprising a methane-containing gas and an oxygen-containing gas to a reaction zone for contact under fermentation conditions with an aqueous medium having a population of methanotrophs therein, said medium containing nutrients for the growth of the population of the methanotroph to provide a methanotroph-rich aqueous medium, said growth of the population of methanotrophs also resulting in the co-production of carbon dioxide, water and heat, and withdrawing unreacted gas from said reaction zone; (b) passing a methane-containing gas and an oxygen-containing gas to a reaction zone for contact under fermentation conditions with at least a portion of the methanotroph-rich aqueous medium, said medium having a limitation of at least one nutrient required for the growth of the population of the methanotrophs to create nutrient limited conditions that inhibit the growth of the population of methanotrophs and to cause production of polyhydroxyalkanoate—by the methanotrophs and the co-production of carbon dioxide, water and heat, and withdrawing unreacted gas from said reaction zone; and (c) separating the polyhydroxyalkanoate-containing methanotrophs from the aqueous medium of step (b), wherein for at least a portion of the duration of each steps (a) and (b):
   i. the rate of passing at least one substrate gas-containing gas to the reaction zone in each of steps (a) and (b) is at substrate-diffusion conditions;
   ii. in at least one of steps (a) and (b) a portion of the aqueous medium is continuously withdrawn from the reaction zone and contacted with a stripping gas to remove carbon dioxide and provide a carbon dioxide-lean aqueous medium; and
   iii. passing at least a portion of the carbon dioxide-lean aqueous medium to the reaction zone of at least one of steps (a) and (b).

2. The process of claim 1 wherein the substrate-limiting gas comprises methane-containing gas.

3. The process of claim 2 wherein the rate of passing methane-containing gas to the reaction zone in at least one of steps (a) and (b) is modulated to provide a substantially stable molar concentration of methane in the unreacted gases.

4. The process of claim 1 wherein the methane-containing feed contains hydrogen sulfide and the aqueous medium absorb absorbs at least a portion of the hydrogen sulfide to provide an unreacted gas stream containing a reduced concentration of hydrogen sulfide.

5. The process of claim 1 wherein the reaction zone of at least one of steps (a) and (b) is a deep tank, bubble column reaction zone characterized in substantially uniform liquid composition and substantially non-uniform gas composition over the height of the reaction zone, and at least a portion of said substrate-containing gas is introduced in a lower portion of the reaction zone.

6. The process of claim 1 wherein rate of withdrawal of the broth in step (ii) is sufficient to remove an amount of carbon dioxide equivalent to at least about 40 percent of the carbon dioxide produced by the metabolic activity in the reaction zone.

7. The process of claim 6 wherein rate of withdrawal of the broth in step (ii) is sufficient to remove between 50 and 75 percent of the carbon dioxide produced by the metabolic activity in the reaction zone.

8. The process of claim 2 wherein at least one oxygenated C1 compound is added to the reaction zone of step (a) when the rate of passing methane-containing gas to the reaction zone is no longer under methane-diffusion conditions.

9. The process of claim 1 wherein the portion of the carbon dioxide-lean aqueous medium passed to the reaction zone of at least one of steps (a) and (b) is cooled.

10. The process of claim 1 wherein steps (a) and (b) are performed sequentially in a reactor vessel.

11. The process of claim 1 wherein each of steps (a) and (b) are performed in separate reactor vessels.

12. The process of claim 11 wherein a portion of the aqueous medium in the reaction zone of step (a) is passed to the reaction zone of step (b).

13. The process of claim 11 wherein at least two reaction zones of step (b) are provided for each reaction zone of step (a) and a portion of the aqueous medium of step (a) is passed to at least one of the step (b) reaction zones at a given time to provide a semi-batch process.

14. The process of claim 13 wherein the portion passed to one of the step (b) reaction zones at a given time is between 25 and 95 percent by volume of the aqueous medium in the reaction zone of step (a), and additional aqueous medium is provided to the reaction zone of step (a) to grow the population of methanotrophs.

15. The process of claim 1 wherein the methane-containing gas comprises biogas.

16. The process of claim 15 wherein the methane-containing gas comprises anaerobic digester gas.

17. The process of claim 15 wherein the methane-containing gas comprises at least one of a landfill gas and a tail gas derived directly or indirectly from another fermentation process.

18. The process of claim 1 wherein the carbon dioxide-lean aqueous medium is subjected to indirect heat exchange with a cooling fluid for further cooling of the carbon dioxide-lean aqueous medium and heating of the cooling fluid.

19. The process of claim 18 wherein the heated cooling fluid from the indirect heat exchange is passed to a heat pump to provide a superheated fluid.

20. The process of claim 19 wherein the superheated fluid is used to heat the stripping gas.

21. The process of claim 19 wherein the superheated fluid is used in the recovery of polyhydroxyalkanoate from methanotrophs.

22. The process of claim 1 wherein aqueous medium is withdrawn from a lower portion of the reaction zone for at least one of step (a) and (b), subjected to flashing conditions to remove a portion of the carbon dioxide therein, and then subjected to contact with a stripping gas.

23. A high productivity process for bioconverting methane to product containing polyhydroxyalkanoate comprising (a) passing a methane-containing gas and an oxygen-containing gas to a reaction zone for contact under fermentation conditions with an aqueous medium having a population of methanotrophs therein, said medium containing nutrients for the growth of the population of the methanotrophs to provide a methanotroph-rich aqueous medium, said growth of the population of methanotrophs also resulting in the co-production of carbon dioxide, water and heat, and withdrawing unreacted gas from said reaction zone; (b) passing a methane-containing gas and an oxygen-containing gas to a reaction zone for contact under fermentation conditions with at least a portion of the methanotroph-rich aqueous medium, said medium having a substantial absence of at least one nutrient required for the growth of the population of the methanotroph, to cause production of polyhydroxyalkanoate and the co-production of carbon dioxide, water and heat, and withdrawing unreacted gas from said reaction zone; and (c) separating the polyhydroxyalkanoate-containing methanotrophs from the aqueous medium of step (b), wherein an oxygenated C1 compound of at least one of methanol and formic acid or water soluble salt thereof is supplied to the aqueous medium in at least one of steps (a) and (b).

24. A high productivity process for bioconverting methane to product containing polyhydroxyalkanoate comprising (a) passing substrate gas comprising a methane-containing gas and an oxygen-containing gas to a reaction zone for contact under fermentation conditions with an aqueous medium having a population of methanotrophs therein, said medium containing nutrients for the growth of the population of the methanotroph to provide a methanotroph-rich aqueous medium, said growth of the population of methanotrophs also resulting in the co-production of carbon dioxide, water and heat, and withdrawing unreacted gas from said reaction zone; (b) passing a methane-containing gas and an oxygen-containing gas to a reaction zone for contact under fermentation conditions with at least a portion of the methanotroph-rich aqueous medium, said medium having a substantial a absence of at least one nutrient required for the growth of the population of the methanotrophs, to cause production of polyhydroxyalkanoate and the co-production of carbon dioxide, water and heat, and withdrawing unreacted gas from said reaction zone; and (c) separating the polyhydroxyalkanoate-containing methanotrophs from the aqueous medium of step (b), wherein for at least a portion of the duration of each steps (a) and (b):
  i. the rate of passing at least one substrate gas-containing gas to the reaction zone in each of steps (a) and (b) is at substrate-diffusion conditions;
  ii. in at least one of steps (a) and (b) a portion of the aqueous medium is continuously withdrawn from the reaction zone and contacted with a semi-permeable membrane to remove carbon dioxide and provide a carbon dioxide-lean aqueous medium; and
  iii. passing at least a portion of the carbon dioxide-lean aqueous medium to the reaction zone of at least one of steps (a) and (b).

* * * * *